United States Patent [19]

Elliott et al.

[11] Patent Number: 5,283,371
[45] Date of Patent: Feb. 1, 1994

[54] INTERMEDIATES USEFUL IN THE PRODUCTION OF PESTICIDES

[75] Inventors: Michael Elliott, Berkeley, Calif.; Norman F. Janes, Luton; Bhupinder P. S. Khambay, Harrow Weald, both of England

[73] Assignee: National Research Development Corporation, England

[21] Appl. No.: 721,149

[22] Filed: Jun. 26, 1991

Related U.S. Application Data

[60] Division of Ser. No. 428,193, Oct. 27, 1989, Pat. No. 5,068,403, which is a continuation of Ser. No. 25,230, Mar. 12, 1987, abandoned.

[30] Foreign Application Priority Data

Mar. 13, 1986 [GB] United Kingdom ............... 8606292
Apr. 18, 1986 [GB] United Kingdom ............... 8609590

[51] Int. Cl.$^5$ ........................................... C07C 43/225
[52] U.S. Cl. ........................................... 568/639
[58] Field of Search ................................ 568/639

[56] References Cited

U.S. PATENT DOCUMENTS

| | | | |
|---|---|---|---|
| 2,312,208 | 2/1949 | Clayton et al. | 562/7 X |
| 2,862,952 | 12/1958 | Washburn et al. | 562/7 X |
| 2,898,365 | 8/1959 | Washburn et al. | 562/7 X |
| 3,030,406 | 4/1962 | Groszos | 562/7 X |
| 3,061,627 | 10/1962 | Lang et al. | 558/286 |
| 3,090,801 | 5/1963 | Washburn et al. | 562/7 X |
| 3,092,652 | 6/1963 | Stern et al. | 558/298 |
| 3,669,926 | 6/1972 | Cyba | 514/64 |
| 4,288,386 | 9/1981 | Soula et al. | 568/639 |
| 4,564,712 | 1/1986 | Kuckertz et al. | 568/639 X |
| 4,766,253 | 8/1988 | Rauber | 568/639 |
| 4,788,349 | 11/1988 | Whittle | 568/639 |
| 4,992,593 | 2/1991 | Siegemund | 568/639 X |
| 5,117,002 | 5/1992 | Buchanan et al. | 568/639 X |
| 5,136,107 | 8/1992 | Stephens et al. | 568/639 |

FOREIGN PATENT DOCUMENTS 1147725 6/1966 United Kingdom .
8504651 10/1985 World Int. Prop. O. .

OTHER PUBLICATIONS

S. Patai, "The Chemistry of the Ether Linkage", paragraph D, pp. 454–455 (1967).
G. C. Finger et al., "Aromatic Fluorine Compounds. Plant Growth Regulations and Intermediates", J. Am. Chem. Soc. vol. 81, pp. 94–101 (1959).
Organic Name Reactions, ONR-91.

*Primary Examiner*—Paul F. Shaver
*Attorney, Agent, or Firm*—Rosenman & Colin

[57] ABSTRACT

A process for the production of a boronic acid of formula III,

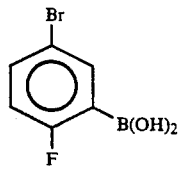

in which an organometallic of formula IV,

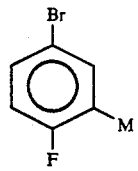

in which formula IV, M represents a metallic moiety such as —MgX, X being a halogen or an alkali metal is treated with a trialkoxy borane of formula B(OR)$_3$, R representing an alkyl group and the product is hydrolysed.

1 Claim, No Drawings

INTERMEDIATES USEFUL IN THE PRODUCTION OF PESTICIDES

CROSS-REFERENCE

This is a division of Ser. No. 428,193 filed Oct. 27, 1989, now U.S. Pat. No. 5,068,403 which is a continuation of Ser. No. 025,230, filed Mar. 12, 1987, now abandoned.

This invention relates to production of intermediates useful in the manufacture of pesticides.

In International Patent Application No. GB 85/00146 there are disclosed methods for the preparation of compounds of formula I $$R_A CR_3 = CR_4 CHDR_B \quad\quad I$$

in which formula:

R$_A$ represents a group ArCR$_1$R$_2$— in which Ar represents a phenyl or naphthyl group optionally substituted by one or more halogen, alkoxy, haloalkoxy, methylenedioxy, C$_1$-C$_6$ alkyl or haloalkyl groups;

R$_1$ and R$_2$ together with the carbon to which they are attached represent a C$_3$-C$_6$ cycloalkyl group optionally substituted by one or more halogen atoms or C$_1$-C$_6$ alkyl groups.

R$_3$ and R$_4$ which may be identical or differ, represent hydrogen, halogen or C$_1$-C$_6$ alkyl groups and R$_B$ represents the residue of an alcohol R$_B$ CHDOH in which D is hydrogen or cyano and of which the [IR, cis]2,2-dimethyl-3-(2,2-dibromovinyl) cyclopropane carboxylic ester is significantly insecticidal, the configuration of R$_A$ and CHDR$_B$ about the double bond being mutually trans.

Compounds I in which R$_B$ represents 4-fluoro-3-phenoxyphenyl are of particular interest and may be prepared inter alia by reaction of the Grignard reagent, 4-fluoro-3-phenoxyphenyl magnesium bromide with a suitable substrate. The bromide required for preparation of this Grignard reagent (5-bromo-2-fluorodiphenyl ether) (II), has, however, been available hitherto only with difficulty.

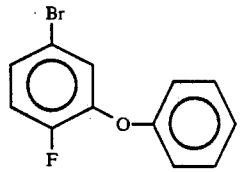

It has now however been found that the bromide and other intermediates can be generated in good yield from 2,4-dibromofluorobenzene, which is available commercially although generally contaminated with the isomer 3,4-dibromofluorobenzene.

Accordingly, the present invention comprises a process for the production of a boronic acid of formula III,

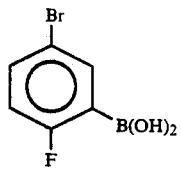

convertible into 5-bromo-2-fluorodiphenyl ether (II), in which an organometallic of formula IV, obtainable from 2,4-dibromofluorobenzene,

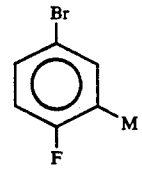

in which formula IV M represents a metallic moiety such as —MgX, (X being a halogen) or an alkali metal such as lithium is treated with a trialkoxy borane of formula B(OR)$_3$, R representing an alkyl group (e.g. a C$_1$-C$_6$ alkyl group which is preferably methyl) and the product is hydrolysed.

It has been found that the boronic acid III crystallizes readily and that the crystals are substantially free of impurities and particularly isomers of the acid III derived from metallation at the 4-bromo position of 2,4-dibromofluorobenzene or derived from 3,4-dibromofluorobenzene impurity in the starting material.

Accordingly, in a preferred embodiment of the present process, the boronic acid III is crystallised and the crystals are isolated prior to further treatment.

The amount of the metal or metal alkyl used to treat 2,4-dibromofluorobenzene and thus produce the organometallic IV may be reduced to 80% or less of the stoichiometric amount. Under these conditions bromine at the 2-position in 2,4-dibromofluorobenzene may react in preference to bromine at the 4-position and 2,4-dibromofluorobenzene may react in preference to 3,4-dibromofluorobenzene present as a contaminant, so that a good yield of the desired isomer of formula IV is obtained. Amounts less than 60% of stoichiometric are undesirable as the yield is unnecessarily decreased.

The boronic acid III may be converted into the intermediate 5-bromo-2-fluorodiphenyl ether II, by oxidation, suitably using hydrogen peroxide, to the corresponding phenol V the corresponding alkali metal phenoxide of which VI reacts with a halobenzene, in which the halogen is chlorine, bromine or iodine, under Ullman conditions e.g. in the presence of a copper catalyst such as copper bronze or a Cu$^I$ or Cu$^{II}$ halide to give II

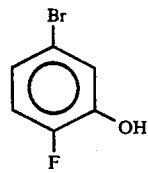

The present invention includes in a further aspect an organometallic of formula IV, a boronic acid III, a phenol V, a phenoxide VI and processes as hereinbefore described for the conversion of 2,4-dibromofluorobenzene to the organometallic IV, of the boronic acid III to the phenol V, of the phenol V to the phenoxide VI and of the phenoxide VI to the intermediate 5-bromo-2-fluorodiphenyl ether.

The invention is illustrated by the following Example:

Dihydroxy-(5-bromo-2-fluorophenyl)-borane

A solution of 2,4-dibromofluorobenzene (12.7 g, containing 30% 3,4-dibromofluorobenzene) in dry tetrahydrofuran (THF) (10 ml) is added over 5 min to a stirred suspension of magnesium turnings (1.15 g) in dry THF (50 ml) under an atmosphere of nitrogen and cooled in a water bath. After 1 hour, when all the magnesium has reacted, this reagent is added over 20 min to a stirred solution of trimethoxyborane (7 ml) in dry diethyl ether (80 ml) under an atmosphere of nitrogen and cooled at −78° C. The mixture is stirred at −78° C. for a further 15 min. and glacial acetic acid (6 ml) added followed by water (50 ml). The mixture is warmed to room temperature, extracted with diethyl ether (×3), washed with water, dried and the solvent evaporated under reduced pressure. The residue is stirred with carbon tetrachloride (30 ml) and then cooled at 0° C. The crystals of dihydroxy-(5-bromo-2-fluorophenyl)-borane are filtered off and washed with a little carbon tetrachloride. Yield 2.8 g m.p.t. 173°–174° C.

5-Bromo-2-fluorophenol

To a stirred solution of dihydroxy-(5-bromo-2-fluorophenyl)borane (2 g) in diethyl ether (10 ml) is added chloroform (10 ml) and 30% hydrogen peroxide (10 ml). The mixture is stirred for 18 hours at room temperature, diluted with water, extracted with diethyl ether (×3) and back extracted with 2M NaOH (or, in an alternative embodiment producing relatively increased yields, with stronger sodium hydroxide, e.g. 5M NaOH). The aqueous layer is acidified with aqueous 2N HCl extracted with diethyl ether (×3), dried and the solvent evaporated to give 5-bromo-2-fluorophenol, yield 1.25 g. A sample is purified by t.l.c. on silica gel eluted with 30% diethyl ether in petroleum ether b.p. 60°–80° C. $n_D 1.5564$. Alternatively, the product is distilled b.p. 52°–54°/0.2 mm Hg.

5-Bromo-2-fluoro-diphenyl ether

Sodium hydride (0.2 g of 60% dispersion in oil) is added in small portions to a stirred solution of 5-bromo-2-fluorophenol (1 g) in 2-methoxyethyl ether (1 ml) under nitrogen and cooled in a water bath. Cuprous bromide (0.09 g) and a solution of bromobenzene (1.5 ml) in 2-methoxymethyl ether (2 ml) were added and the mixture refluxed for 6 hours. The mixture was poured onto water, extracted with petroleum ether b.p. 60°–80° (×3), washed with water, dried, solvent evaporated and the residue distilled at 0.02 mm Hg b.pt. 80°–82° C. $n_D$ 1.5708, Yield 0.55 g.

We claim:

1. A process for the production of 5-bromo-2-fluorodiphenyl ether, comprising oxidizing a boronic acid of formula III

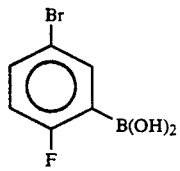

III to 5-bromo-2-fluorophenol, forming the alkali metal phenoxide of said 5-bromo-2-fluorophenol and reacting the alkali metal phenoxide with a halobenzene under Ullmann conditions.

* * * * *

UNITED STATES PATENT AND TRADEMARK OFFICE
CERTIFICATE OF CORRECTION

PATENT NO. : 5,283,371
DATED : February 1, 1994
INVENTOR(S) : Michael Elliot et al It is certified that error appears in the above-indentified patent and that said Letters Patent is hereby corrected as shown below:

On the title page, item [73], the name of the assignee should read -- British Technology Group Limited --.

Signed and Sealed this

Twenty-first Day of March, 1995

Attest:

BRUCE LEHMAN

*Attesting Officer*     *Commissioner of Patents and Trademarks*